US012788467B2

(12) United States Patent
Hull et al.

(10) Patent No.: US 12,788,467 B2
(45) Date of Patent: Nov. 10, 2026

(54) SYSTEMS AND METHODS FOR PERCUTANEOUS ACCESS AND FORMATION OF ARTERIOVENOUS FISTULAS

(71) Applicant: Avenu Medical, Inc., San Juan Capistrano, CA (US)

(72) Inventors: Jeffrey E. Hull, Midlothian, VA (US); David T. Aldridge, Dana Point, CA (US); Seth A. Foerster, San Clemente, CA (US); Brad M. Kellerman, Escondido, CA (US); Gene B. Reu, San Clemente, CA (US); Mark A Ritchart, Murrieta, CA (US); David K. Wrolstad, Fallbrook, CA (US)

(73) Assignee: Avenu Medical, Inc., San Clemente, CA (US)

( * ) Notice: Subject to any disclaimer, the term of this patent is extended or adjusted under 35 U.S.C. 154(b) by 0 days.

(21) Appl. No.: 18/531,471

(22) Filed: Dec. 6, 2023

(65) Prior Publication Data

US 2024/0099760 A1 Mar. 28, 2024

Related U.S. Application Data

(62) Division of application No. 16/990,851, filed on Aug. 11, 2020, now Pat. No. 11,877,785, which is a (Continued)

(51) Int. Cl.
*A61B 18/04* (2006.01)
*A61B 17/11* (2006.01)

(Continued)

(52) U.S. Cl.
CPC ............ *A61B 18/085* (2013.01); *A61B 17/11* (2013.01); *A61B 18/04* (2013.01); *A61B 18/082* (2013.01);

(Continued)

(58) Field of Classification Search
CPC ....... A61B 18/085; A61B 17/11; A61B 18/04; A61B 18/082; A61B 2017/1107;

(Continued)

(56) References Cited

U.S. PATENT DOCUMENTS 5,290,278 A 3/1994 Anderson
5,425,731 A 6/1995 Daniel et al.

(Continued)

*Primary Examiner* — Eugene T Wu
(74) *Attorney, Agent, or Firm* — Stout, Uxa & Buyan, LLP; Donald E. Stout

(57) ABSTRACT

A device and method for creating an arteriovenous (AV) fistula includes a proximal base having a distal diagonal end surface and a distal tip connected to the proximal base and movable relative to the proximal base. The distal tip has a proximal diagonal end surface. A heating assembly, including an energized heating element, is disposed one of the distal diagonal end surface and the proximal diagonal end surface. A passive heating assembly is disposed on the mating diagonal end surface. The distal diagonal end surface and the proximal diagonal end surface are adapted to contact opposing sides of a tissue portion to create a fistula. The angle of the proximal diagonal end surface matches the angle of the distal diagonal end surface, so that the two surfaces match one another during deployment.

20 Claims, 15 Drawing Sheets

Related U.S. Application Data division of application No. 14/641,190, filed on Mar. 6, 2015, now Pat. No. 10,772,672.

(60) Provisional application No. 61/949,166, filed on Mar. 6, 2014.

(51) Int. Cl.
*A61B 18/08* (2006.01)
*A61B 18/00* (2006.01)
*A61B 90/00* (2016.01)

(52) U.S. Cl.
CPC ................. *A61B 2017/1107* (2013.01); *A61B 2017/1139* (2013.01); *A61B 2018/00404* (2013.01); *A61B 2018/0063* (2013.01); *A61B 2018/00648* (2013.01); *A61B 2018/00702* (2013.01); *A61B 2018/00714* (2013.01); *A61B 2018/00791* (2013.01); *A61B 2090/064* (2016.02)

(58) Field of Classification Search
CPC .. A61B 2017/1139; A61B 2018/00404; A61B 2018/0063; A61B 2018/00648; A61B 2018/00702; A61B 2018/00714; A61B 2018/00791; A61B 2090/064
See application file for complete search history.

(56) References Cited

U.S. PATENT DOCUMENTS

| | | | | |
|---|---|---|---|---|
| 5,830,222 | A | 11/1998 | Makower | |
| 5,830,224 | A | 11/1998 | Cohn et al. | |
| 6,024,739 | A | 2/2000 | Ponzi | |
| 6,068,637 | A | 5/2000 | Popov et al. | |
| 6,068,638 | A | 5/2000 | Makower | |
| 6,071,292 | A | 6/2000 | Makower et al. | |
| 6,083,223 | A | 7/2000 | Baker | |
| 6,099,542 | A | 8/2000 | Cohn et al. | |
| 6,190,353 | B1 | 2/2001 | Makower et al. | |
| 6,235,027 | B1 | 5/2001 | Herzon | |
| 6,283,983 | B1 | 9/2001 | Makower et al. | |
| 6,302,875 | B1 | 10/2001 | Makower et al. | |
| 6,330,884 | B1 | 12/2001 | Kim | |
| 6,375,615 | B1 | 4/2002 | Flaherty et al. | |
| 6,379,319 | B1 | 4/2002 | Garibotto et al. | |
| 6,398,797 | B2 | 6/2002 | Bombard et al. | |
| 6,409,721 | B1 | 6/2002 | Wheelock et al. | |
| 6,464,665 | B1 | 10/2002 | Heuser | |
| 6,533,778 | B2 | 3/2003 | Herzon | |
| 6,561,998 | B1 | 5/2003 | Roth et al. | |
| 6,579,311 | B1 | 6/2003 | Makower | |
| 6,613,081 | B2 | 9/2003 | Kim et al. | |
| 6,616,675 | B1 | 9/2003 | Evard et al. | |
| 6,699,245 | B2 | 3/2004 | Dinger et al. | |
| 6,699,709 | B1 | 3/2004 | Bonde et al. | |
| 6,709,444 | B1 | 3/2004 | Makower | |
| 6,726,677 | B1 | 4/2004 | Flaherty et al. | |
| 6,863,684 | B2 | 3/2005 | Kim et al. | |
| 6,908,463 | B2 | 6/2005 | Treat et al. | |
| 6,929,009 | B2 | 8/2005 | Makower et al. | |
| 7,056,325 | B1 | 6/2006 | Makower et al. | |
| 7,074,220 | B2 | 7/2006 | Hill et al. | |
| 7,159,592 | B1 | 1/2007 | Makower et al. | |
| 7,191,015 | B2 | 3/2007 | Lamson et al. | |
| 7,316,655 | B2 | 1/2008 | Garibotto et al. | |
| 7,351,247 | B2 | 4/2008 | Kupiecki et al. | |
| 7,387,636 | B2 | 6/2008 | Cohn et al. | |
| 7,588,566 | B2 | 9/2009 | Treat et al. | |
| 7,729,738 | B2 | 6/2010 | Flaherty et al. | |
| 7,846,172 | B2 | 12/2010 | Makower | |
| 7,988,690 | B2 | 8/2011 | Chanduszko et al. | |
| 8,236,014 | B2 | 8/2012 | Brenneman et al. | |
| 8,721,639 | B2 | 5/2014 | Mirizzi et al. | |
| 8,834,518 | B2 | 9/2014 | Faller et al. | |
| 2003/0040764 | A1 | 2/2003 | Adams | |
| 2003/0144660 | A1 | 7/2003 | Mollenauer | |
| 2003/0225426 | A1 | 12/2003 | Hill et al. | |
| 2003/0229344 | A1 | 12/2003 | Dycus et al. | |
| 2004/0073238 | A1 | 4/2004 | Makower | |
| 2004/0204725 | A1 | 10/2004 | Bayer | |
| 2005/0033330 | A1 | 2/2005 | Vargas et al. | |
| 2005/0038457 | A1 | 2/2005 | Vargas et al. | |
| 2005/0251167 | A1 | 11/2005 | Voegele et al. | |
| 2006/0020265 | A1* | 1/2006 | Ryan .................. | A61B 18/1442 606/50 |
| 2006/0111704 | A1 | 5/2006 | Brenneman et al. | |
| 2006/0142788 | A1 | 6/2006 | Wilson et al. | |
| 2006/0189979 | A1 | 8/2006 | Esch et al. | |
| 2006/0217706 | A1 | 9/2006 | Lau | |
| 2006/0217709 | A1* | 9/2006 | Couture ............. | A61B 18/1442 606/51 |
| 2007/0112348 | A1 | 5/2007 | Eggers et al. | |
| 2007/0175963 | A1* | 8/2007 | Bilotti .................. | A61B 17/115 227/179.1 |
| 2007/0276363 | A1 | 11/2007 | Patton et al. | |
| 2008/0187989 | A1 | 8/2008 | McGreevy et al. | |
| 2008/0312651 | A1 | 12/2008 | Pope et al. | |
| 2009/0048589 | A1 | 2/2009 | Takashino et al. | |
| 2009/0312783 | A1 | 12/2009 | Whayne et al. | |
| 2010/0152723 | A1 | 6/2010 | Esch et al. | |
| 2010/0204698 | A1 | 8/2010 | Chapman et al. | |
| 2011/0011916 | A1 | 1/2011 | Levine | |
| 2011/0095067 | A1 | 4/2011 | Ohdaira | |
| 2011/0251608 | A1 | 10/2011 | Timm et al. | |
| 2011/0251609 | A1 | 10/2011 | Johnson et al. | |
| 2011/0306959 | A1* | 12/2011 | Kellerman ............. | A61B 17/11 606/28 |
| 2011/0306968 | A1 | 12/2011 | Beckman et al. | |
| 2011/0306993 | A1 | 12/2011 | Hull et al. | |
| 2012/0078246 | A1 | 3/2012 | Mirizzi et al. | |
| 2012/0302935 | A1 | 11/2012 | Miller et al. | |
| 2012/0316550 | A1 | 12/2012 | Lau et al. | |
| 2013/0123827 | A1 | 5/2013 | Kellerman et al. | |
| 2013/0281998 | A1* | 10/2013 | Kellerman ............. | A61B 18/04 606/29 |
| 2014/0039478 | A1 | 2/2014 | Hull et al. | |
| 2014/0094791 | A1 | 4/2014 | Hull et al. | |
| 2014/0142561 | A1* | 5/2014 | Reu ...................... | A61B 18/082 606/29 |

* cited by examiner

SYSTEMS AND METHODS FOR PERCUTANEOUS ACCESS AND FORMATION OF ARTERIOVENOUS FISTULAS

STATEMENT OF RELATED CASES

This application is a divisional application under 35 U.S.C. 120 of U.S. patent application Ser. No. 16/990,851, entitled Systems and Methods for Percutaneous Access and Formation of Arteriovenous Fistulas, filed on Aug. 11, 2020 and currently pending, which is a divisional application under 35 U.S.C. 120 of U.S. patent application Ser. No. 14/641,190, entitled Systems and Methods for Percutaneous Access and Formation of Arteriovenous Fistulas, filed on Mar. 6, 2015, issued as U.S. Pat. No. 10,772,672 and currently pending, which in turn claims the benefit under 35 U.S.C. 119(e) of the filing date of Provisional U.S. Application Ser. No. 61/949,166, entitled Systems and Methods for Percutaneous Access and Formation of Arteriovenous Fistulas, filed on Mar. 6, 2014. The above referenced applications are herein expressly incorporated by reference, in their entirety.

BACKGROUND OF THE INVENTION

In the body, various fluids are transported through conduits throughout the organism to perform various essential functions. Blood vessels, arteries, veins, and capillaries carry blood throughout the body, carrying nutrients and waste products to different organs and tissues for processing. Bile ducts carry bile from the liver to the duodenum. Ureters carry urine from the kidneys to the bladder. The intestines carry nutrients and waste products from the mouth to the anus.

In medical practice, there is often a need to connect conduits to one another or to a replacement conduit to treat disease or dysfunction of the existing conduits. The connection created between conduits is called an anastomosis.

In blood vessels, anastomoses are made between veins and arteries, arteries and arteries, or veins and veins. The purpose of these connections is to create either a high flow connection, or fistula, between an artery and a vein, or to carry blood around an obstruction in a replacement conduit, or bypass. The conduit for a bypass is a vein, artery, or prosthetic graft.

An anastomosis is created during surgery by bringing two vessels or a conduit into direct contact. The vessels are joined together with suture or clips. The anastomosis can be end-to-end, end-to-side, or side-to-side. In blood vessels, the anastomosis is elliptical in shape and is most commonly sewn by hand with a continuous suture. Other methods for anastomosis creation have been used including carbon dioxide laser approaches and a number of methods using various connected prostheses, clips, and stents.

An arterio-venous fistula (AVF) is created by connecting an artery to a vein, and to create a leak-free blood flow path between them. This type of connection is used for hemodialysis, to increase exercise tolerance, to keep an artery or vein open, or to provide reliable access for chemotherapy.

An alternative is to connect a prosthetic graft from an artery to a vein for the same purpose of creating a high flow connection between artery and vein. This is called an arterio-venous graft, and requires two anastomoses. One is between artery and graft, and the second is between graft and vein.

A bypass is similar to an arteriovenous graft. To bypass an obstruction, two anastomoses and a conduit are required. A proximal anastomosis is created from a blood vessel to a conduit. The conduit extends around the obstruction, and a second distal anastomosis is created between the conduit and vessel beyond the obstruction.

As noted above, in current medical practice, it is desirable to connect arteries to veins to create a fistula for the purpose of hemodialysis. The process of hemodialysis requires the removal of blood from the body at a rapid rate, passing the blood through a dialysis machine, and returning the blood to the body. The access to the blood circulation is achieved with 1) catheters placed in large veins, 2) prosthetic grafts attached to an artery and a vein, or 3) a fistula where an artery is attached directly to the vein.

Hemodialysis is required by patients with kidney failure. A fistula using native blood vessels is one way to create high blood flow. The fistula provides a high flow of blood that can be withdrawn from the body into a dialysis machine to remove waste products and then returned to the body. The blood is withdrawn through a large access needle near the artery and returned to the fistula through a second large return needle. These fistulas are typically created in the forearm, upper arm, less frequently in the thigh, and in rare cases, elsewhere in the body. It is important that the fistula be able to achieve a flow rate of 500 ml per minute or greater in order for the vein to mature or grow. The vein is considered mature once it reaches >4 mm and can be accessed with a large needle. The segment of vein in which the fistula is created needs to be long enough (>6 cm) to allow adequate separation of the access and return needle to prevent recirculation of dialyzed and non-dialyzed blood between the needles inserted in the fistula.

Fistulas are created in anesthetized patients by carefully dissecting an artery and vein from their surrounding tissue, and sewing the vessels together with fine suture or clips. The connection thus created is an anastomosis. It is highly desirable to be able to make the anastomosis quickly, reliably, with less dissection, and with less pain. It is important that the anastomosis is the correct size, is smooth, and that the artery and vein are not twisted.

SUMMARY OF THE INVENTION

The present invention eliminates the above described open procedures, reduces operating time, and allows for consistent and repeatable fistula creation.

The present invention comprises a device for creating a percutaneous arteriovenous (AV) fistula, which comprises a proximal base having a distal diagonal end surface and a distal tip connected to the proximal base and movable relative to the proximal base. The distal tip has a proximal diagonal end surface. A first heating assembly, comprising an embedded energized heating element, is disposed on at least one of the distal diagonal end surface and the proximal diagonal end surface. A second heating assembly, comprising a passive non-energized heat spreader, is disposed on the other distal diagonal end surface. The distal diagonal end surface and the proximal diagonal end surface are adapted to contact opposing sides of a tissue portion to create the fistula. The distal diagonal end surface is oriented at an angle of 15-90 degrees relative to a longitudinal axis of the device, and more advantageously at an angle of 15-50 degrees relative to the longitudinal axis. In one particularly optimal configuration, the distal diagonal end surface is oriented at an angle of approximately 23 degrees relative to the longitudinal axis. The angle of the proximal diagonal end surface matches the angle of the distal diagonal end surface, so that the two surfaces match one another while working on opposite sides of the tissue.

A shaft is provided for connecting the distal tip to the proximal base, the shaft being extendable and retractable to extend and retract the distal tip relative to the proximal base. A resilient member in the distal tip manages pressure in the weld.

The proximal diagonal end surface has an embedded heating element disposed thereon. An energized heating element optimally comprises a serpentine configuration within a thermally conductive material. A temperature sensor is disposed near the energized heating element within the conductive material, for providing closed loop temperature control to the heater.

The heat spreader on the proximal face of the distal tip comprises a thermally conductive material which extends across a substantial portion of the diagonal end surface on which it is disposed, the heat spreader being in thermal contact with the energized heating element to conduct heat from the heating element and spread the heat across the diagonal end surface. It is constructed so that it has a thickness approximately equal to a thickness of a vessel in which the device is deployed, this thickness falling within a range of 0.010 inches to 0.060 inches. This is done for optimum radial conduction of heat into tissues. Other configurations optimize heat spreader thickness for insertion. In this application, a smaller profile is desired.

In one configuration, the heat spreader comprises a raised segment forming a rib, for creating a focused heat conduction path through tissue which will quickly cut or ablate tissue. This creates the opening in the fistula through which the blood will flow. After creating the opening, raised segment contacts the heat spreader on the opposing diagonal surface to heat said spreader up to a welding temperature. The tissue between the spreaders are then held at temperatures and pressures required to fuse the tissues together.

The distal tip comprises a distal diagonal outer surface containing an aperture for a through lumen for receiving a guidewire. The distal diagonal surface and the diagonal heat spreader surface are connected with a resilient media which maintains the appropriate pressure for tissue welding.

A position sensor is provided for monitoring movement of the distal tip with respect to the proximal base. This relative position indicates the thickness of tissue captured prior to fistula creation. This information can be valuable in determining if the procedure is proceeding properly. Vessel wall thicknesses are seen on ultrasound and can be estimated. This vessel wall thickness should be reflected in the position sensor. When cutting through tissue, the position sensor should indicate when the tissues are penetrated.

In another aspect of the invention, there is provided a method for creating an arteriovenous (AV) fistula, which comprises steps of selecting an appropriate procedural site having each of a primary vessel and a secondary vessel in close proximity to one another, inserting a piercing device into the primary vessel to pierce the vessel walls, and creating an opening so that the piercing device extends into the adjacent secondary vessel, and advancing a guidewire until the guidewire is positioned in a blood flow path of the secondary vessel sufficiently to allow the piercing device to be removed. The piercing device is then withdrawn. A proximal end of the guidewire is loaded into the distal lumen of a device for dilating the guidewire's path through both vessels. The proximal end of the dilator is then loaded into the lumen of a sheath and advanced through both vessels. The dilator is then removed and replaced by the device. The distal tip of the device is then advanced to place the proximal and distal diagonals in the first and second vessels. The sheath is then removed so that the proximal and distal diagonal jaw faces directly oppose the first and second vessel walls.

At this juncture, a heater on the diagonal distal surface of the proximal base is seated against an inner wall of the first vessel surrounding the opening. The distal tip is retracted so that the heat spreader on the diagonal proximal surface of the distal tip seats against an inner wall of the second vessel surrounding the opening, thereby capturing the walls of the first and second vessel between the facing angled surfaces of each of the distal tip and the proximal base, respectively.

The distal tip and the proximal base are pulled together, and at the same time energy is applied to the heating element on the distal diagonal surface of the proximal base. The resultant applied heat and motion causes the raised rib on the heater to cut or ablate through tissue until the raised rib contacts the heat spreader on the distal tip. The raised rib allows tissue to reside between the embedded heater and the heat spreader. The proximal heater transfers heat to the distal heat spreader by direct conduction from the contact of the raised rib with the distal heat spreader The distal heat spreader floats on a resilient base contained within the tip while in contact with the proximal heater. Sufficient energy is applied to weld tissue. The device is then removed leaving a welded fistula with blood flow sufficient to support dialysis.

In still another aspect of the invention, a method of creating a passage between adjacent primary and secondary vessels is disclosed, comprising a step of positioning a sheath across both vessels at the fistula site, introducing the device into the sheath so that its distal mechanisms are placed appropriately in relation to the vessel walls, removing the sheath, actuating a cutting mechanism in the device to open a communicating aperture from the primary to secondary vessel, and actuating a welding mechanism in the device to weld both vessels together.

In yet another embodiment of the invention, there is provided an apparatus which comprises a first tissue weld member having a first contact surface configured to contact a surface of a first tissue wall. The first tissue weld member includes an electrical conductor beneath the first contact surface. A tubular member is coupled to the first tissue weld member, and is configured to operatively couple the electrical conductor to a power supply. A second tissue weld member has a second contact surface configured to contact a surface of a second tissue wall, the second contact surface being configured to be aligned with the first contact surface to position the surface of the first tissue wall and the surface of the second tissue wall between the first contact surface and the second contact surface such that when a current is conveyed from the power supply to the electrical conductor, the first tissue wall and the second tissue wall are welded together.

The power supply is configured to control the current to produce a heat flow between the surface of the first tissue wall and the surface of the second tissue wall sufficient to denature a protein in at least one of the first tissue wall or the second tissue wall.

The first contact surface, in exemplary embodiments, is flat, and the second contact surface is flat. The first contact surface includes a first alignment portion having a first shape, and the second contact surface includes a second alignment portion having a second shape that corresponds to the first shape. In an exemplary embodiment, the first alignment portion includes a rectangular protrusion and the second alignment portion defines a rectangular recess corresponding to the rectangular protrusion. The first tissue weld member and the second tissue weld member are configured to be compressed against each other to exert a compression force against the first tissue wall and the second tissue wall. The second tissue weld member is configured to maintain the compression force within a range.

In still another aspect of the invention, there is disclosed a method, which comprises steps of advancing a tubular member within a first blood vessel, a first tissue weld member coupled to an end portion of the tubular member, and moving a second tissue weld member within a second blood vessel to align a first contact surface of the first weld member with a second contact surface of the second member, such that a portion of the first blood vessel and a portion of the second blood vessel are between the first contact surface and the second contact surface. Further steps include compressing the portion of the first blood vessel and the portion of the second blood vessel between the first contact surface and the second contact surface, and conveying a current to the first weld member to cause a heat flow between the first contact surface and the second contact surface, the heat flow sufficient to weld the first blood vessel and the second blood vessel together.

The conveying the current step produces the heat flow sufficient achieve a temperature within the portion of the first blood vessel and a portion of the second blood vessel of between about 150 degrees Celsius and 600 degrees Celsius. The moving the second tissue weld member within the second blood vessel step includes aligning a first alignment portion of the first tissue weld member with a second alignment portion of the second tissue weld member, a shape of the first alignment portion corresponding to a shape of the second alignment portion.

In exemplary embodiments, the first alignment portion includes a rectangular protrusion and the second alignment portion defines a rectangular recess corresponding to the rectangular protrusion, and the moving the second tissue weld member step includes moving the rectangular protrusion at least partially within the rectangular recess. The compressing the portion of the first blood vessel and the portion of the second blood vessel step includes limiting a compression force exerted against the first blood vessel and the second blood vessel.

The method further comprises moving the first tissue weld member away from the portion of the first blood vessel, and moving the second tissue weld member away from the portion of the first blood vessel. The first contact surface and the second contact surface may include a coating formulated to reduce tissue adherence.

In another aspect of the invention, there is provided an apparatus, which comprises a first tissue weld member having a first contact surface and a weld element, a tubular assembly coupled to the first tissue weld member, the tubular assembly configured to move the first tissue weld member within a first bodily vessel, the tubular assembly configured to couple the electrical conductor to a power supply, and a second tissue weld member having a second contact surface. The second tissue weld member is configured to be moved within a second bodily vessel to move the second contact surface relative to the first contact surface to compress a first vessel wall of the first bodily vessel and a second vessel wall of the second bodily vessel between the first contact surface and the second contact surface, such that when a current is conveyed from the power supply to the weld element, the first vessel wall and the second vessel wall are welded together.

The weld element is configured to thermally weld the first vessel wall and the second vessel wall together, and is further configured, in exemplary embodiments, to produce a heat flow between the first vessel wall and the second vessel wall sufficient to denature a protein in at least one of the first vessel wall or the second vessel wall. The weld element may be a heating element disposed beneath the first contact surface. The first tissue weld member and the second tissue weld member are collectively configured to maintain a compression force within a range. The second tissue weld member includes a resilient member configured to limit the compression force. The first contact surface includes a first alignment portion having a first shape, and the second contact surface includes a second alignment portion having a second shape that corresponds to the first shape, the first alignment portion being aligned with the second alignment portion when the second contact surface is moved relative to the first contact surface to compress a first vessel wall of the first bodily vessel and a second vessel wall of the second bodily vessel between the first contact surface and the second contact surface.

Another aspect of the invention involves an apparatus, which comprises a first tissue weld member having a first contact surface and a weld element, the first contact surface including a first alignment portion, the first tissue weld member coupled to a first tubular member, the first tubular member configured to be moved within a first bodily vessel to place the first contact surface against a first vessel wall of the first bodily vessel. A second tissue weld member has a second contact surface, the second contact surface including a second alignment portion corresponding to the first alignment portion, the second tissue weld member being coupled to a second tubular member. The second tubular member is configured to be moved within a second bodily vessel to align the first alignment portion with the second alignment portion, with a first vessel wall of the first bodily vessel and a second vessel wall of the second bodily vessel being disposed between the first contact surface and the second contact surface such that when the weld element is actuated the first vessel wall and the second vessel wall are welded together.

The first contact surface is parallel to the second contact surface when the first alignment portion and the second alignment portion are aligned. The first contact surface is axially aligned with the second contact surface when the first alignment portion and the second alignment portion are aligned. The first alignment portion has a first shape, and the second alignment portion has a second shape that corresponds to the first shape. At least a portion of the first tubular member is parallel to a portion of the second tubular member. The portion of the first tubular member is coaxial with a portion of the second tubular member. At least a portion of the second tubular member is movably disposed within a portion of the first tubular member.

The first tissue weld member and the second tissue weld member are collectively configured to maintain a compression force against the first vessel wall and the second vessel wall. The weld element is configured to thermally weld the first vessel wall and the second vessel wall together. The weld element is also configured to produce a heat flow between the first vessel wall and the second vessel wall sufficient to denature a protein in at least one of the first vessel wall or the second vessel wall.

The invention, together with additional features and advantages thereof, may best be understood by reference to the following description taken in conjunction with the accompanying illustrative drawings.

DETAILED DESCRIPTION OF THE INVENTION

Notation and Nomenclature

Figures 1A, 1B:
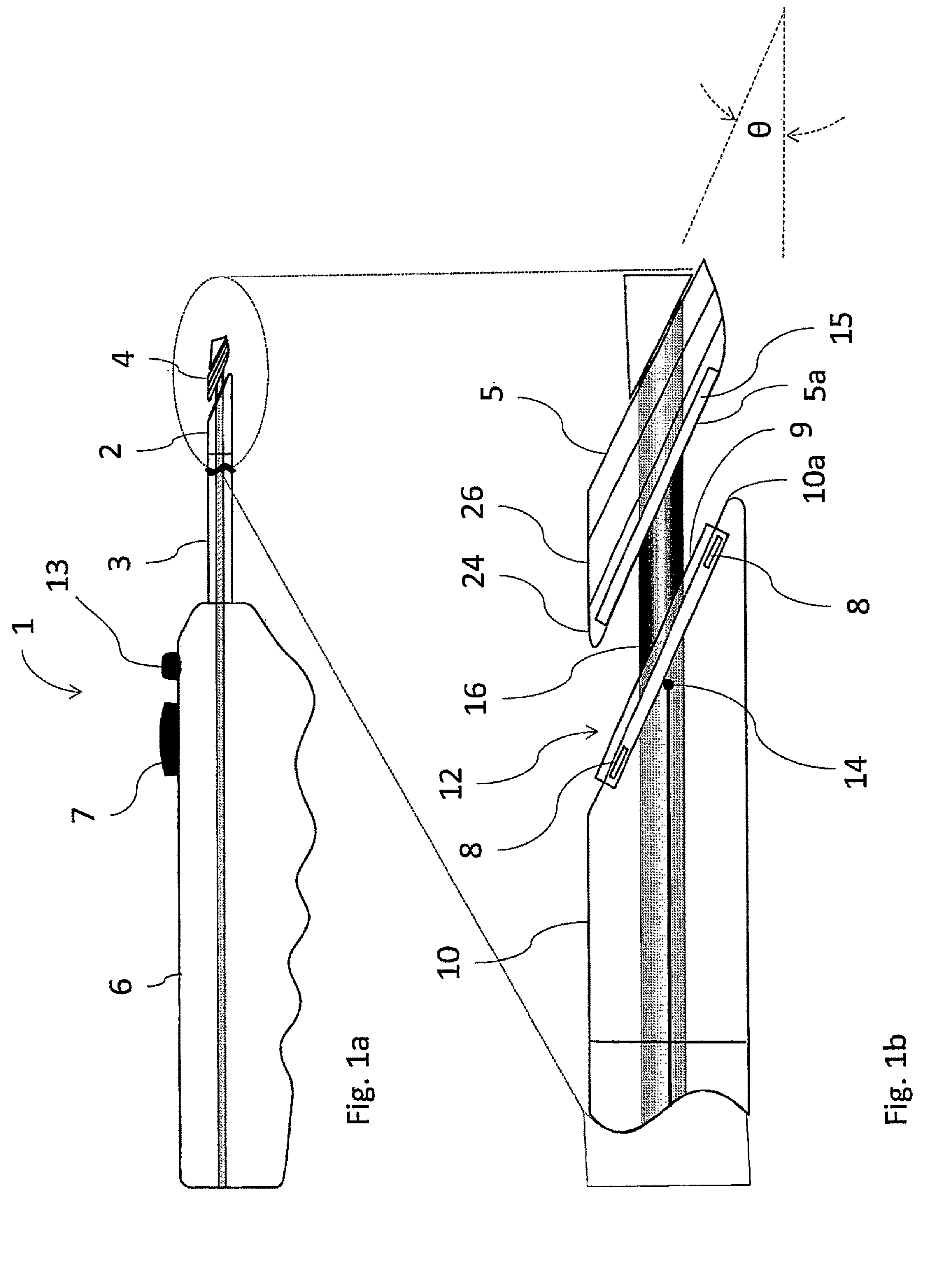
FIG. 1*a* is an elevational view of the handle portion of a device constructed in accordance with one embodiment of the present invention.
FIG. 1*b* is an elevational enlarged view of the circled distal working portion of the device of FIG. 1*a;*

Certain terms are used throughout the following description and claims to refer to particular system components. As one skilled in the art will appreciate, companies that design and manufacture medical devices may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection, or through an indirect connection via other devices, components, and connections. Further, the terms "proximal" and distal are intended to refer to proximity relative to a bone anchor applicator. Thus, if a first device is distal and a second device is proximal, the second device is nearer to the bone anchor applicator than the first device.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent application and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Before the various embodiments are described in detail, it is to be understood that this invention is not limited to particular variations set forth herein as various changes or modifications may be made, and equivalents may be substituted, without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

The technology disclosed herein would have a broad application in vessel surgery for an animal, such as a human. This includes surgery of ducts, ureters, arteries, veins, grafts, or any other tubular structure that transports material. Some of these procedures include, but are not limited to, artery to venous fistula creation, vascular repair, coronary artery bypass graft surgery, femoral popliteal bypass, transjugular intrahepatic portosystemic shunt, splenorenal shunt, or a mesocaval shunt.

Referring now more particularly to the drawings, as illustrated in FIGS. 1*a* and 1*b*, one embodiment of the inventive intraluminal anastomotic device 1 comprises four main components, including a proximal heating assembly 2, a proximal shaft 3, a distal heating assembly 4, and a handpiece 6. The distal heating assembly 4 comprises a distal tip 5 and heat spreader 24. The handpiece 6 comprises a tip actuation button 7 and a release button 13. The proximal heating assembly 2 is constructed of a proximal base 10 that is cut at an angle θ at the distal end.

On the diagonal surface 10*a* of the proximal base 10, a heating element 8 is embedded. The proximal base 10 is typically constructed of a thermally insulating material that is resistive to high temperatures. An embedded heater 12 is used to compress and heat the tissue to create coaptation of vessel tissues. This process is known as tissue welding or tissue fusion. In one embodiment, the embedded heater 12 is constructed of a thermally conductive material with the resistive heating element embedded therein.

Figure 4B:
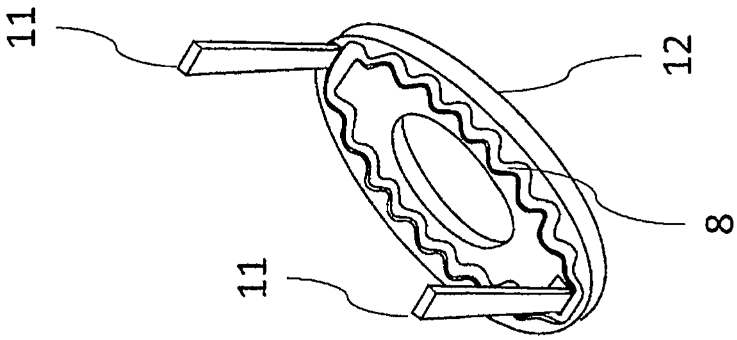
FIG. 4*b* is an isometric view showing the embedded heater.
Figure 4A:
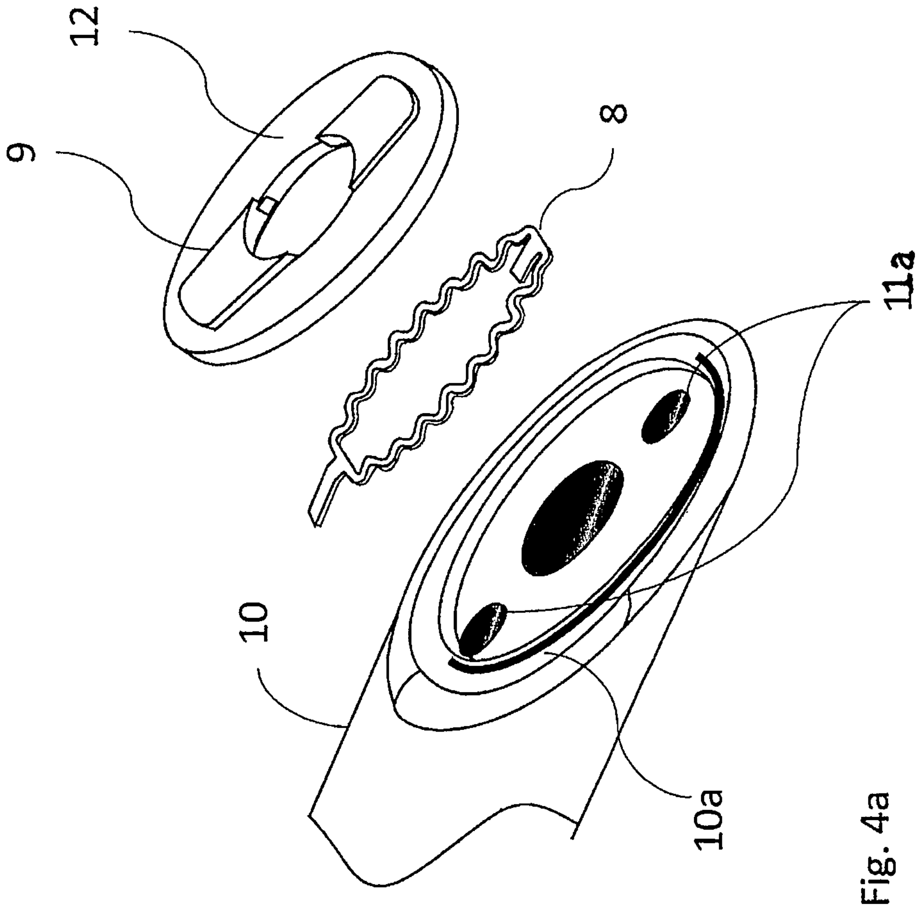
FIG. 4*a* is an exploded isometric view illustrating an embodiment of the proximal base and particularly showing the assembly of the embedded heater.
Figure 5:
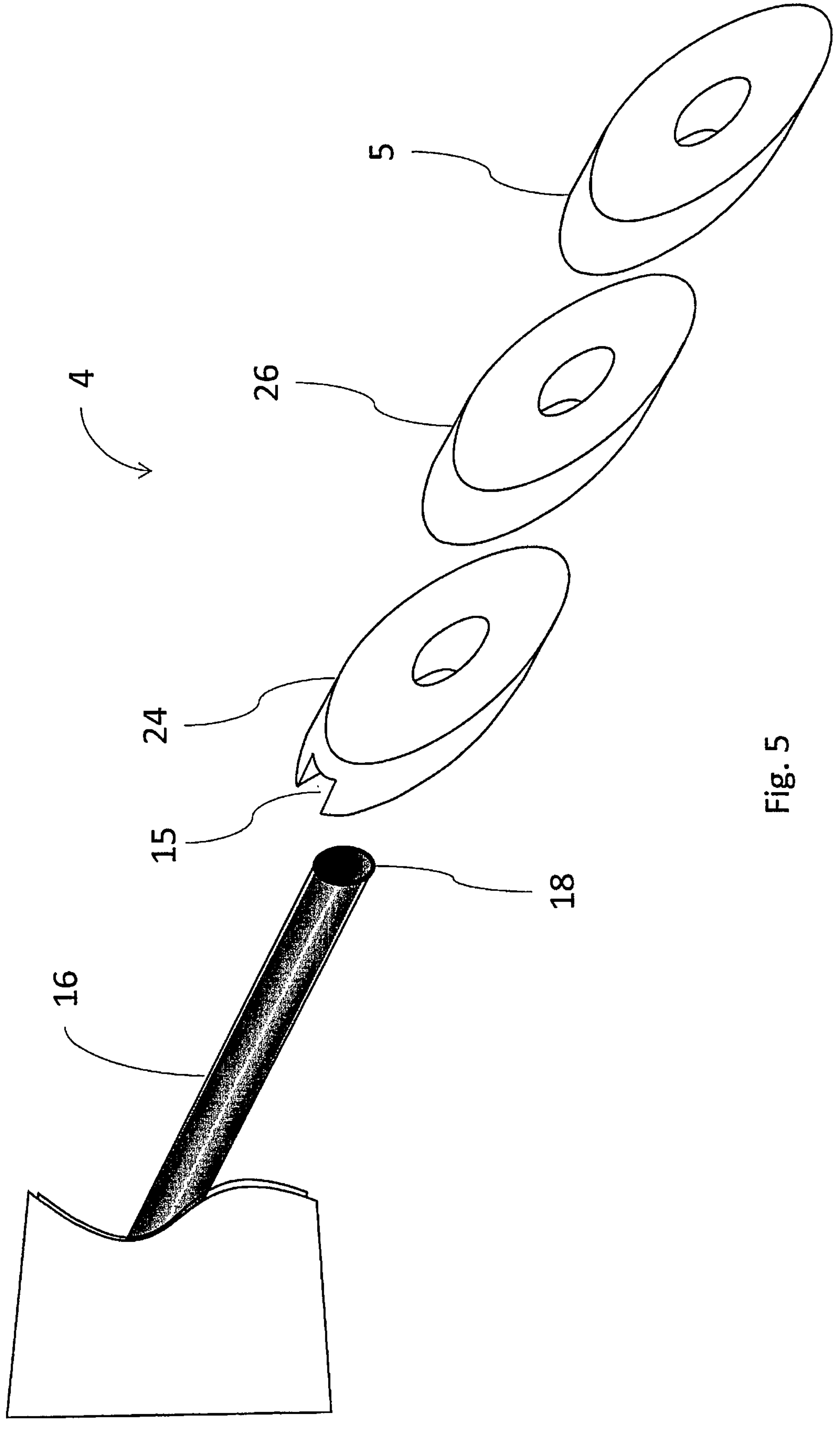
FIG. 5 is an exploded isometric view of the distal tip showing the heat spreader, the resilient member, and the guidewire lumen.
Figure 6:
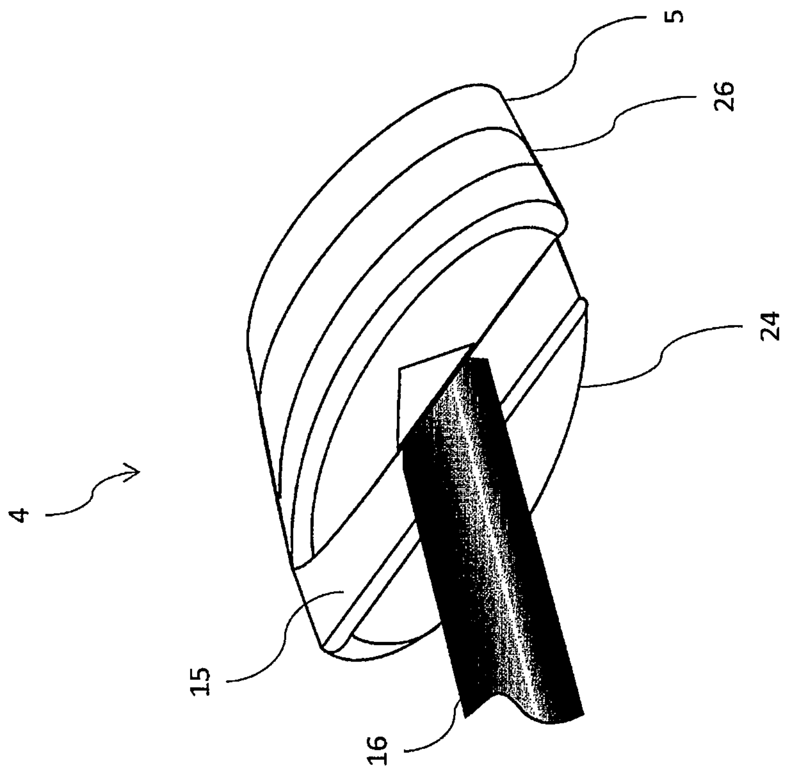
FIG. 6 is an isometric view of the distal tip.

FIG. 4*a* and FIG. 4*b* show the construction of embedded heater or heating surface 12. Heating element 8 takes on a serpentine configuration to increase length and, therefore, surface area leading to higher energy densities. Heating element 8 is attached inside of a mating cavity from which power attachment leads 11 extend and are inserted into lumens 11*a* where they are attached to conductors that extend back to handpiece 6. Ribs 9 are a part of embedded heater 12 and are also made of a conductive material. Ribs 9 will heat up to initially cut tissue prior to welding. Ribs 9 move into rib relief 15 on heat spreader 24 to cut tissue (see FIG. 5).

Figure 9:
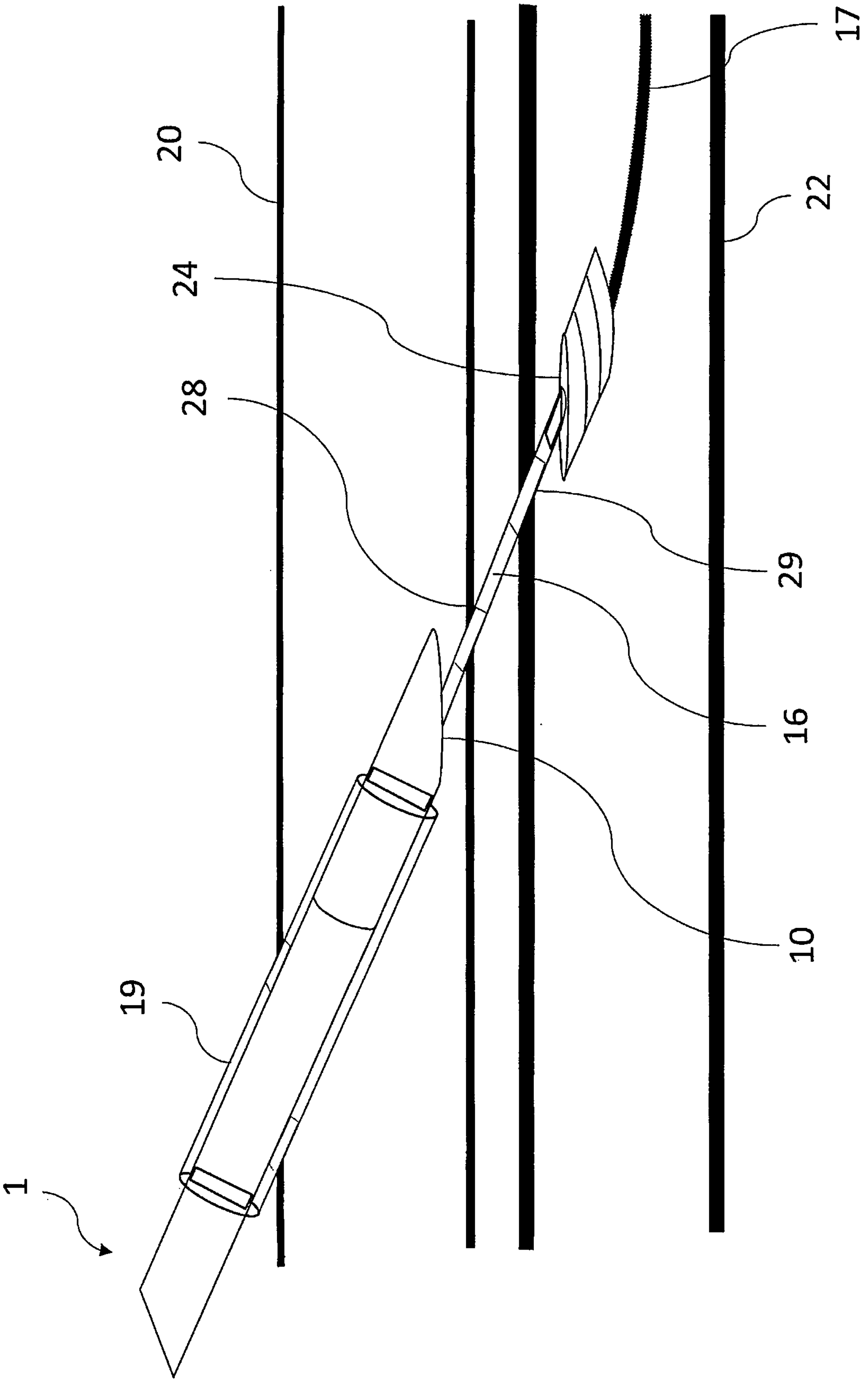
FIG. 9 is a diagram depicting the retraction of the sheath and placement of the device within vessels.

The proximal base 10 is configured with at least one thermocouple or temperature sensor 14 shown in FIG. 1*b* to monitor the temperature near the active heating element 8, and provides a means for closed loop temperature control to optimize tissue welding and cutting. The proximal base is designed to reside in primary vessel 20 (FIG. 9) during deployment.

Figure 2A:
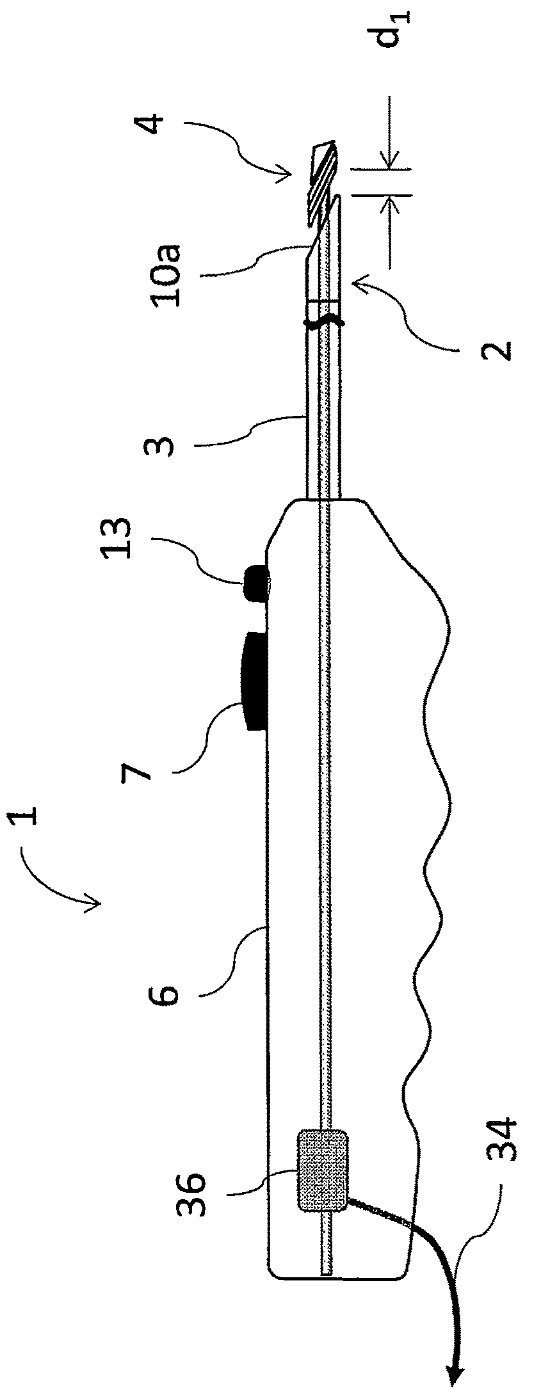
FIG. 2*a* is an elevational view of an embodiment like that shown in FIGS. 1*a*-1*b*, with the distal end in a first working configuration.
Figure 2B:
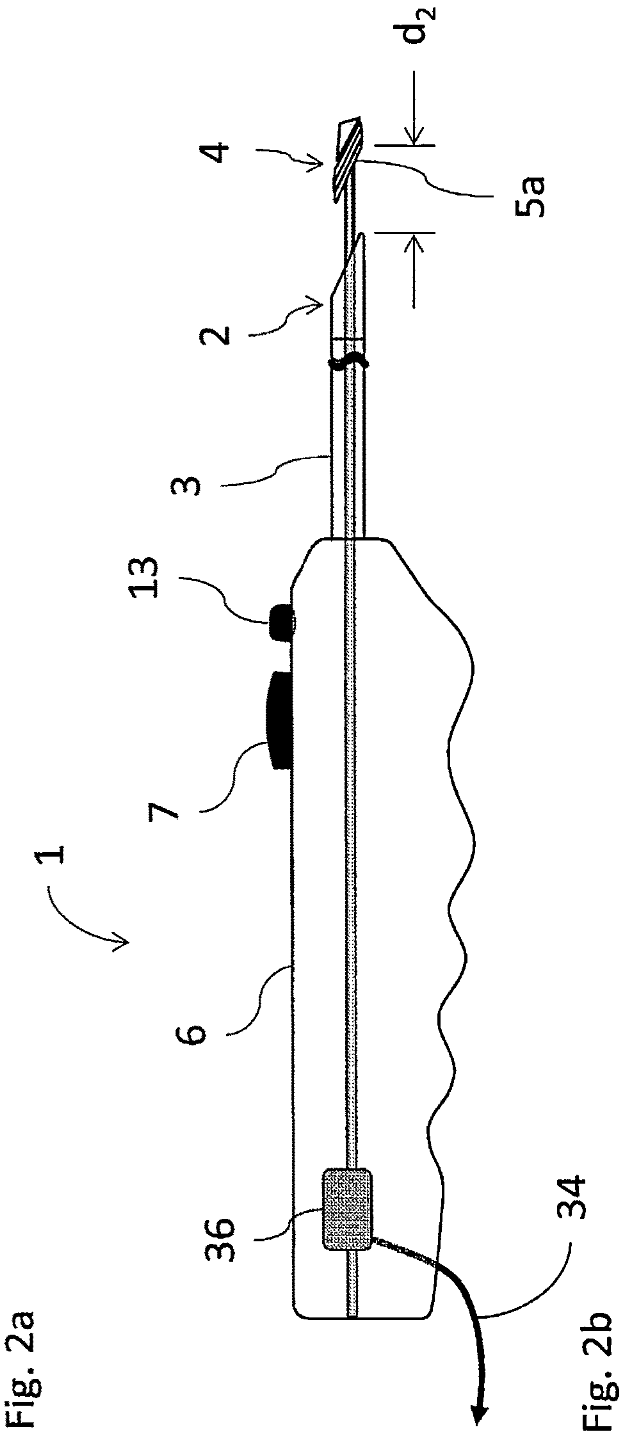
FIG. 2*b* is an elevational view similar to FIG. 2*a*, with the distal end in a second working configuration.
Figure 3:
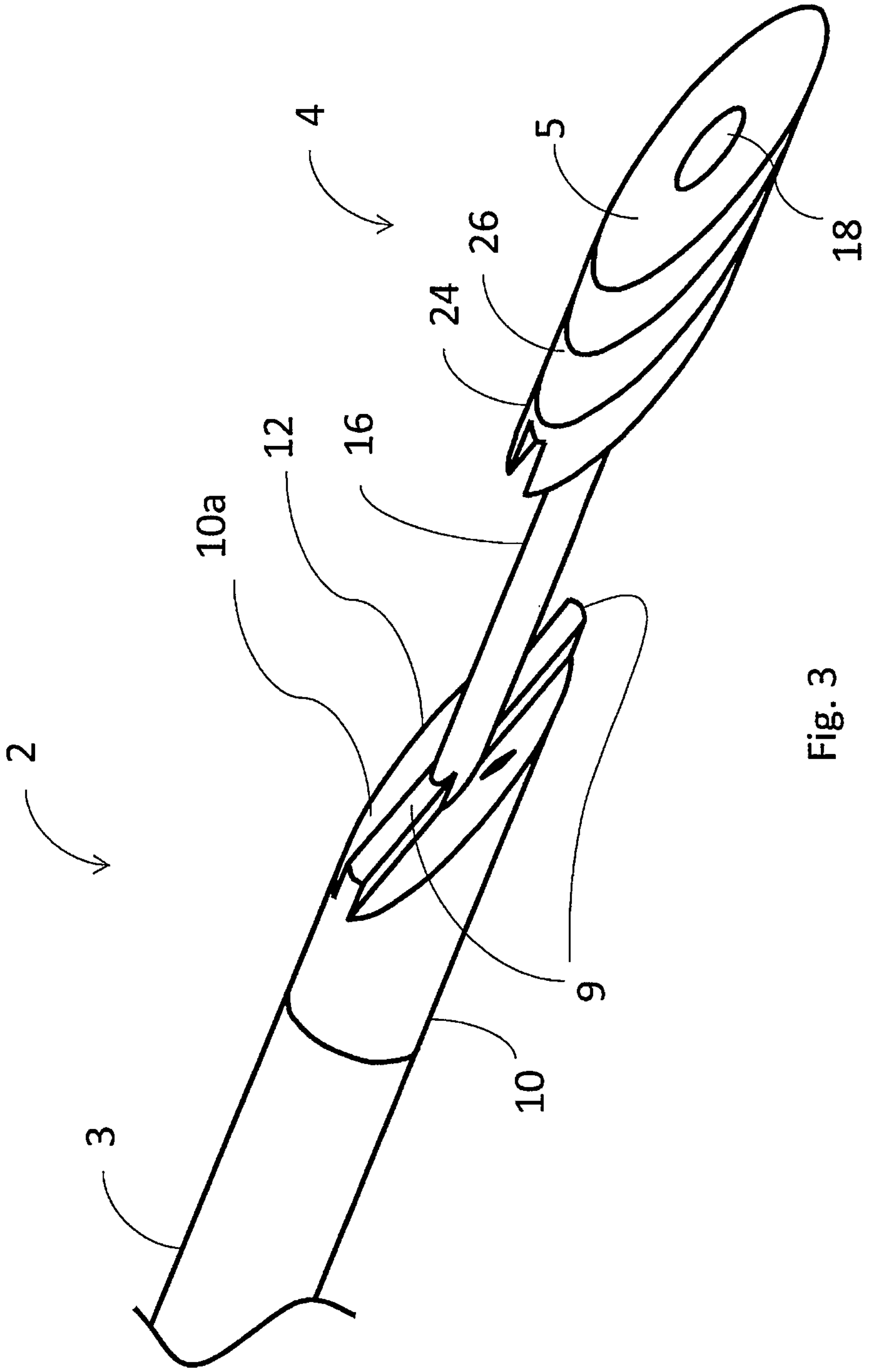
FIG. 3 is an isometric view of one embodiment of the device shown in FIGS. 1*a*-2*b;*

As illustrated in FIGS. 1-3, the distal tip 5 terminates in a diagonal surface at angle θ. A guidewire lumen 18 extends through the center of the distal tip 5, as shown in FIG. 3. Distal heating assembly 4 is designed to reside in secondary vessel 22 (FIG. 9) during deployment. Distal tip 5 moves with inner tube 16 to desired distance d as shown in FIGS. 2*a* and 2*b*. Movement is generally to bring distal tip 5 toward the proximal heating assembly 2, thereby capturing vessel wall tissues between the two components 2 and 4 for the purpose of welding said tissues together. A proximal end surface 5*a* of the distal heating assembly 4 is angled to precisely match the angle θ of the proximal heating assembly 2. This is designed so that components 2 and 4 capture vessel tissue between parallel surfaces.

Figure 12:
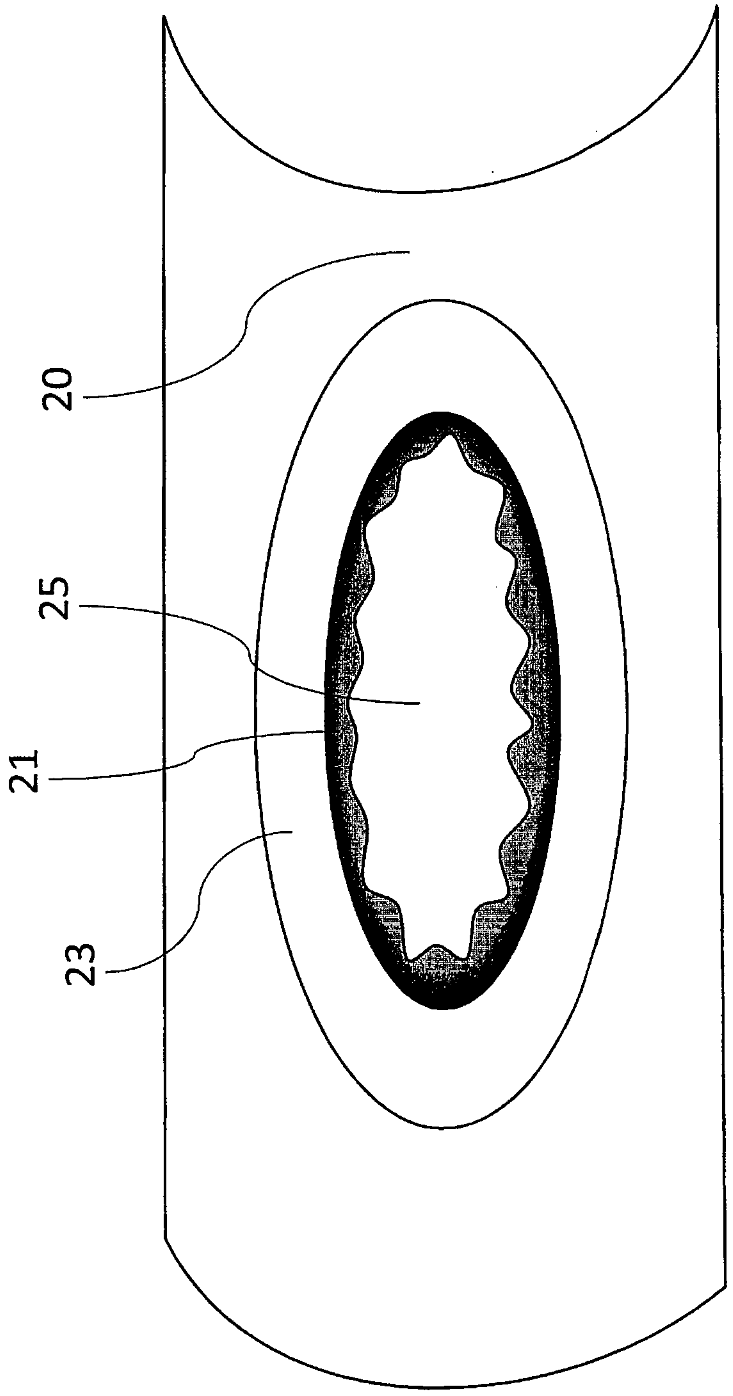
FIG. 12 is a diagram of an anastomosis creating using the devices and methods disclosed in the present application.

The proximal base 10 is configured as shown in FIGS. 4*a* and 4*b*. The proximal base 10 is configured to receive heating element 8 (FIGS. 4*a* and 4*b*), which is covered by heating surface 12. The heating surface 12 is comprised of a thermally conductive material which draws heat from heating element 8. Power attachment points 11 ensure that heating element 8 may be energized. The heating surface 12 transfers heat into the adjoining vessels to create a weld and/or cut tissue to create an anastomosis or fistula 25 (FIG. 12). The size and shape of heating surface 12 mirrors the anastomosis to be created. The thickness of the heating surface 12 is approximately the thickness of the vessel in which the weld is being created. However, the thickness may be increased or decreased to control the amount of heat that is conducted into the surrounding tissue. Typical thickness of the heating surface ranges from 0.010 inches to 0.060 inches (FIGS. 3*a*-3*b*, 4*a*-4*c*).

The embodiment illustrated in FIGS. 2*a* and 2*b* provides distal tip feedback, wherein movement of the distal heating assembly 4, from $d_2$ to $d_1$, is converted to a signal by a position sensor 36 within the handpiece 6, or alternatively, outside of handpiece 6. This movement can then be displayed and/or utilized for a control algorithm. A signal that relays the absolute position of the distal heating assembly 4 from the position sensor 36 to a display device (not shown) of some type, through an output signal cable 34 is valuable for verifying the tip position throughout the procedure and for determining the thickness of the tissue between the tip and base of the catheter before, during, and after the formation of the fistula 25 (FIG. 12). The tissue thickness is related to the distance measurement by the equation $T=d \sin \theta$. The tissue thickness before the procedure can be correlated to the length of the fistula post-procedure. The relative position of the distal heating assembly 4 during the formation of the fistula 25 is also valuable and can be related to the rate of tissue desiccation, cutting and welding. This signal may be used as an input to control heat application. For example, in FIG. 2*a*, the proximal heating assembly 2 and distal heating assembly 4 are spaced by a distance $d_1$, prior to the procedure. Based upon the type and thickness of the tissue through which the anastomosis is being created, and other factors related to functionality and durability of the fistula, tip position after the procedure can provide confirmation that the tissue was properly desiccated and both vessel walls have been cut. The position of the tip can be verified using the sensor(s) 36.

Referring now particularly to FIGS. 7*a* through 10, a method for using the device 1 will be described. To begin the inventive method of intravascular access and communication, the practitioner selects an appropriate procedural site having each of a primary vessel 20 and a secondary vessel 22 in close proximity to one another. In currently preferred approaches, the primary vessel 20 comprises a vein, and the secondary vessel 22 comprises an artery, but the invention is not limited to this arrangement. Initially, a piercing device is inserted into the primary vessel 20 and actuated to pierce the vessel walls and extend into the adjacent secondary vessel 22. Once penetration from primary vessel 20 to secondary vessel 22 has been achieved, guidewire 17 is advanced until positioned in the blood flow path of blood vessel 22 sufficiently to allow the piercing device to be removed while retaining the guidewire's position in blood vessel 22.

Figure 7A:
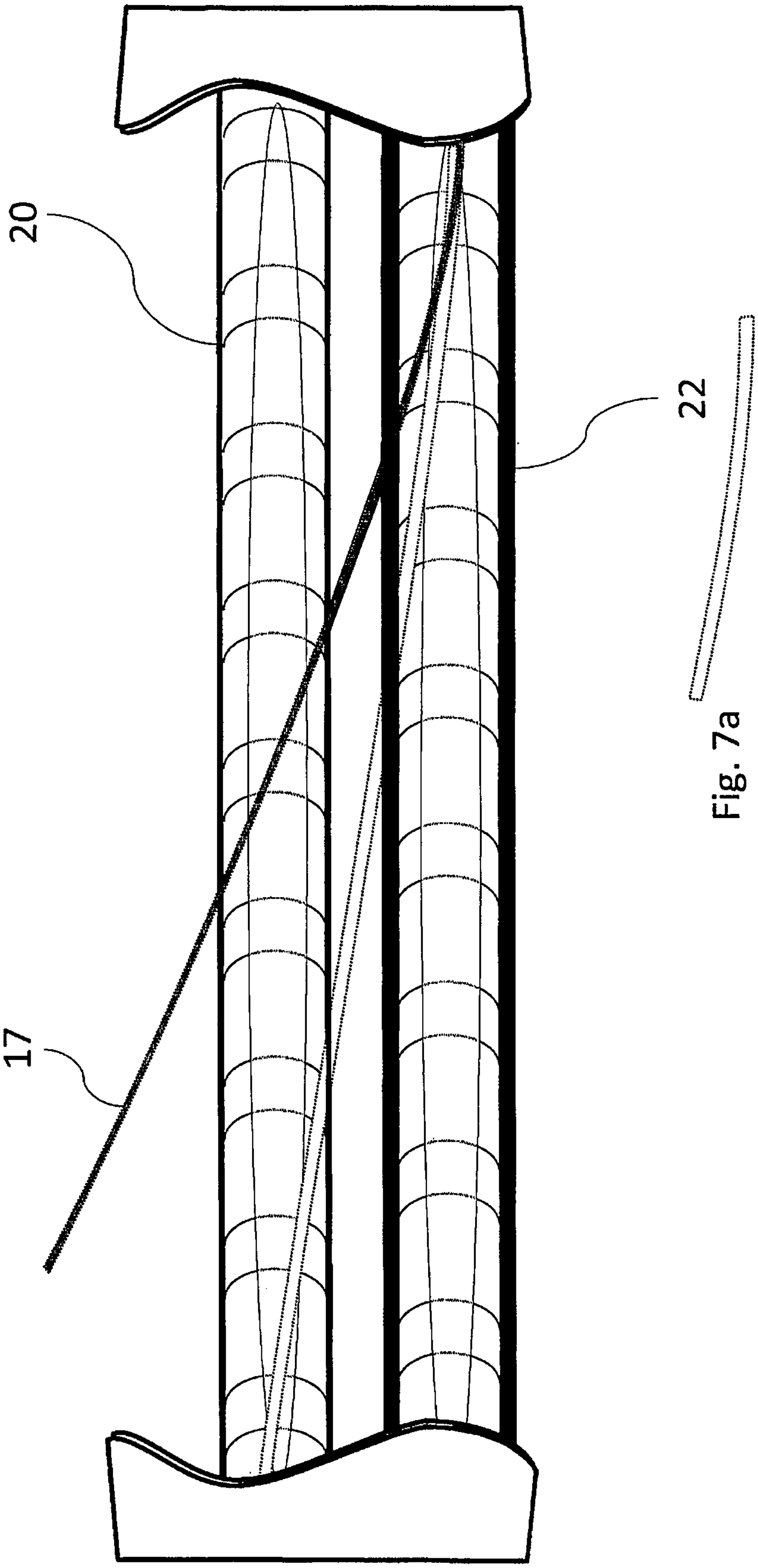
FIG. 7*a* is a diagram depicting the insertion of the guidewire into vessels.
Figure 13:
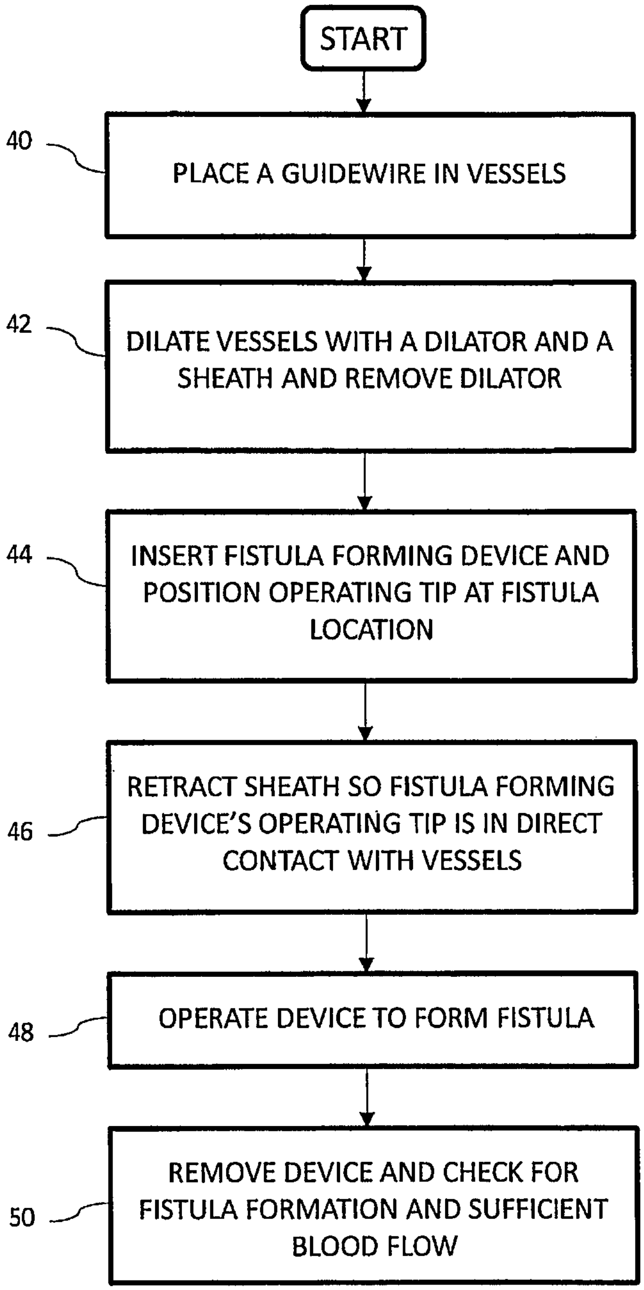
FIG. 13 shows a flow diagram of a medical procedure, using an AV fistula creating device according to at least certain embodiments.

Once guidewire 17 is sufficiently in position as shown in FIG. 7*a*, the practitioner withdraws the piercing device completely from the body, thus leaving the guidewire in the desired position and crossing from primary vessel 20 to secondary vessel 22 as shown in FIG. 7*a* and as described in block 40 of the flow chart illustrated in FIG. 13. One exemplary piercing system and methods is disclosed in co-pending U.S. application Ser. No. 13/668,190, commonly assigned with the present application, and expressly incorporated herein by reference, in its entirety, but any suitable piercing system and method may be used within the scope of the present invention.

Figure 7B:
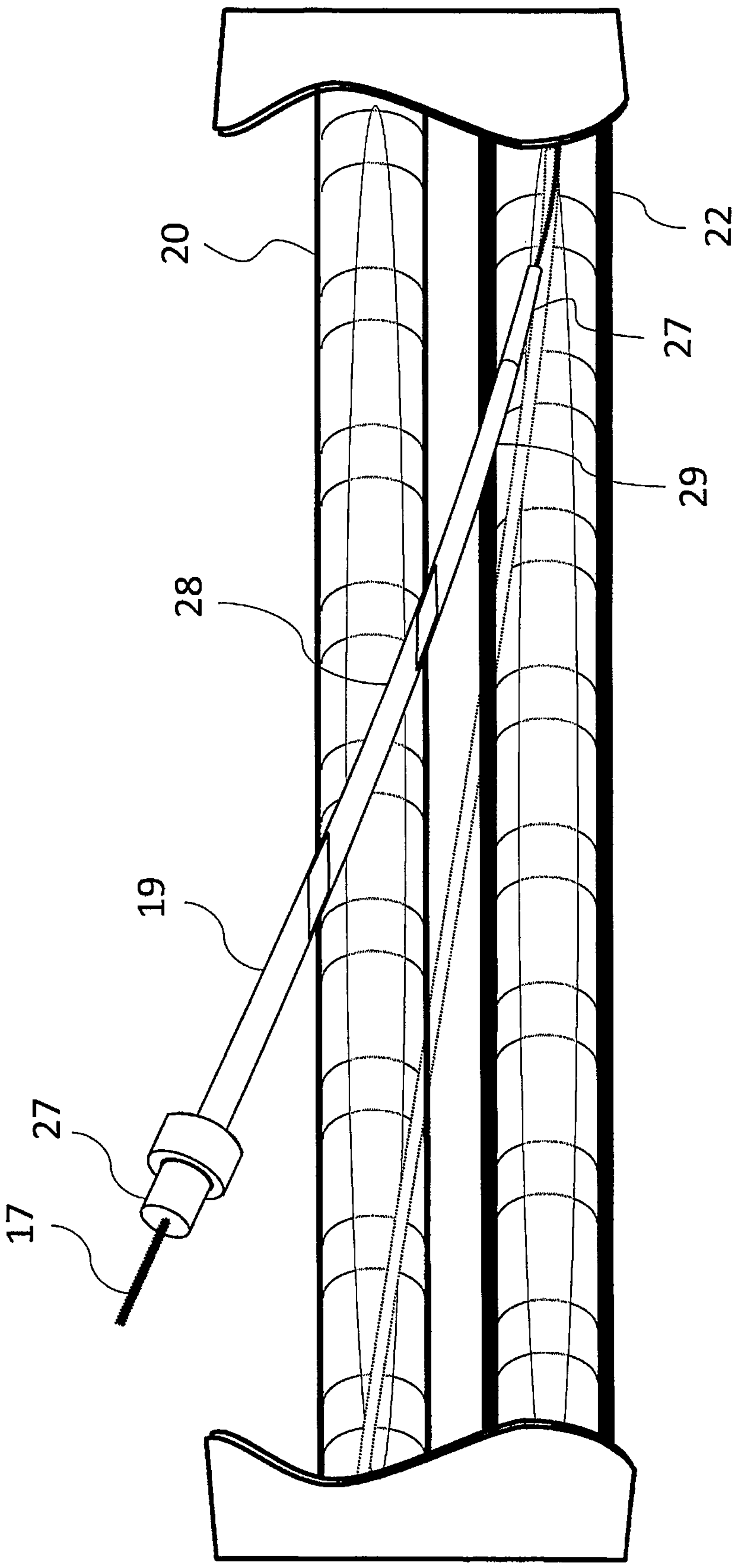
FIG. 7*b* is a diagram depicting the insertion of the dilator into vessels.

Guidewire 17 now provides a track over which the rest of the procedure is performed. First and second vessel openings 28 and 29, respectively must be dilated so that a sheath 19 (FIG. 7*b*) and device 1 may have access. FIG. 7*b* shows a dilator 27 advancing over guidewire 17 to dilate vessel 20 at opening 28 and vessel 22 at opening 29 in anticipation of needing these openings to advance sheath 19 and finally device 1.

Creating openings 28 and 29 in the blood vessels 20 and 22 is a step that is carefully engineered. The tortuosities involved in device access across openings 28 and 29 mandate that both of the dilator 27 and the sheath 19 be made of flexible materials. These tortuosities are further complicated by the need for tapers on the dilator 27 and sheath 19 to be long. Openings 28 and 29 in vessels need to be created in such a way that there are no tears.

Tears in openings 28 and 29 will immediately start to bleed. Blood that enters the fistula site will affect the patency of the tissue weld. Blood needs to stay out of the extra-vessel welding site. Tears created at this point will have minutes to bleed into the extra-vessel space until the procedure advances to tissue welding.

Tears can also cause openings 28 and 29 to not seal sufficiently by device 1. To make openings 28 and 29 without tears, tapers need to be long, smooth, lubricious and, importantly, un-interrupted.

Figure 10:
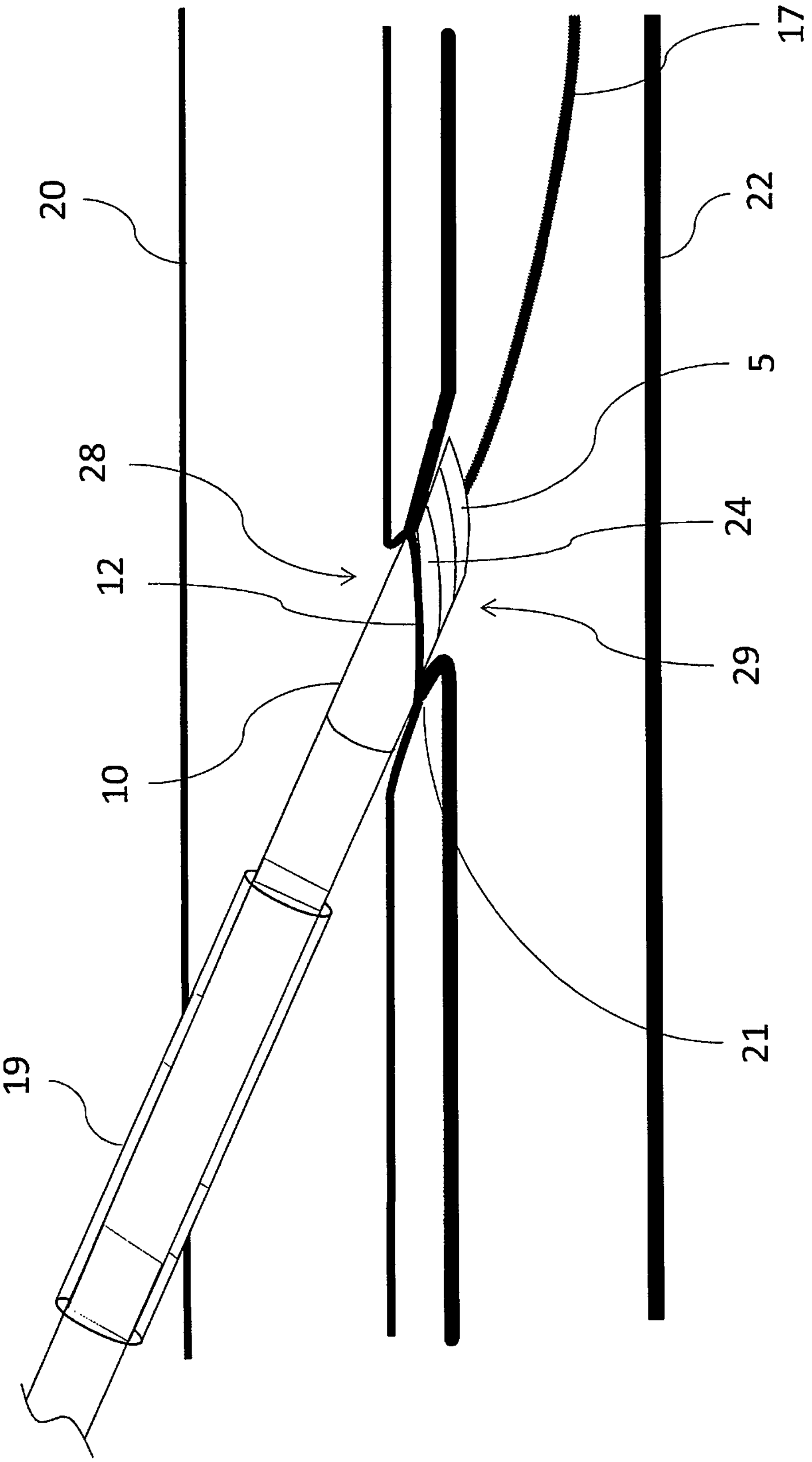
FIG. 10 is a diagram depicting the placement of the device with respect to vessels during welding and cutting.

Devices with tapered tips may also heat up part of their tip in the tissue welding. This, with the combined aggravation of interrupting the blood flow, does cause blood to coagulate within the vessel. The shorter the tip, the less coagulating affects the device during the procedure. It is because of this dynamic that device 1 is shown to have a blunt tip, although variable lengths and tapers can be used to accommodate variable vessel size. As can be seen in FIG. 10, the blunt profile is less intrusive to blood flow.

Figure 7C:
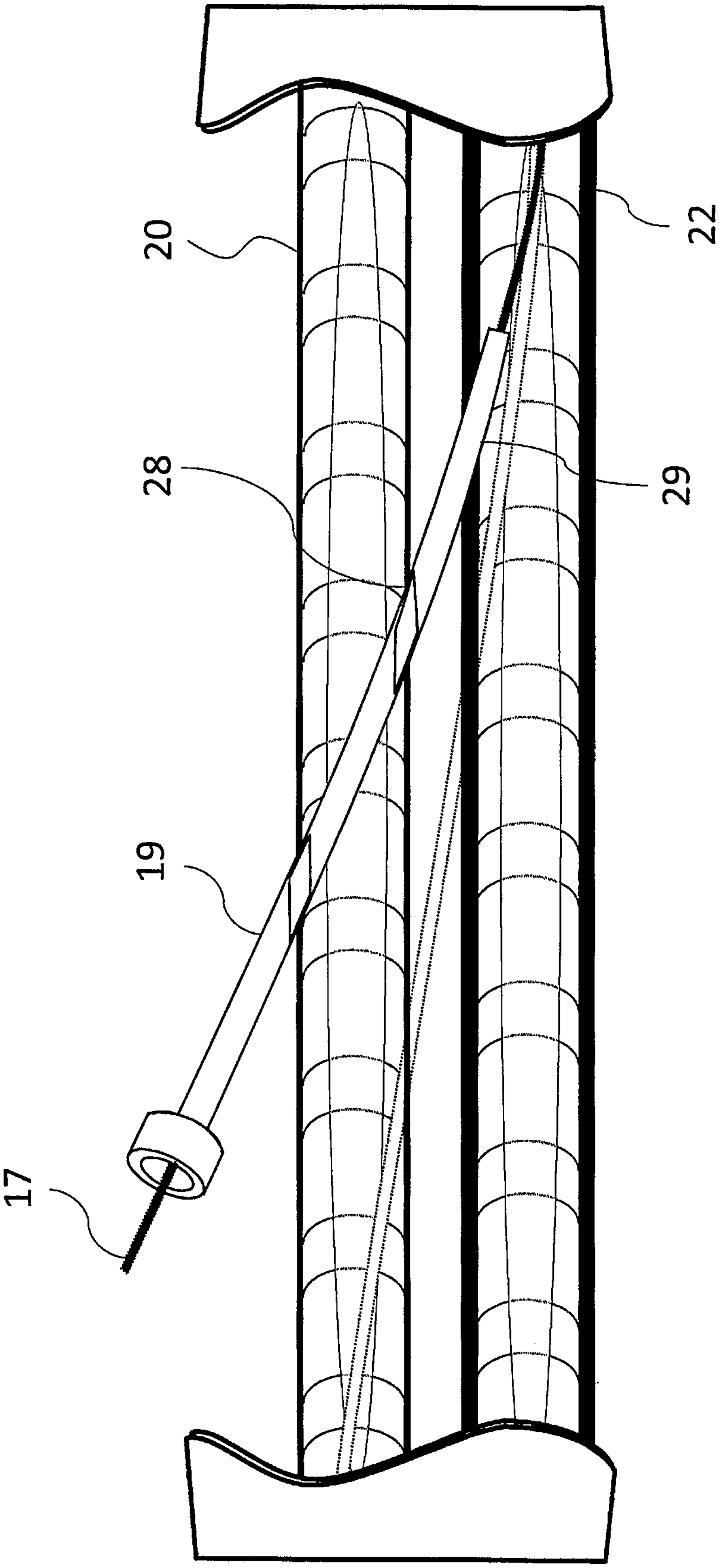
FIG. 7*c* is a diagram depicting the insertion of the sheath into vessels.
Figure 8:
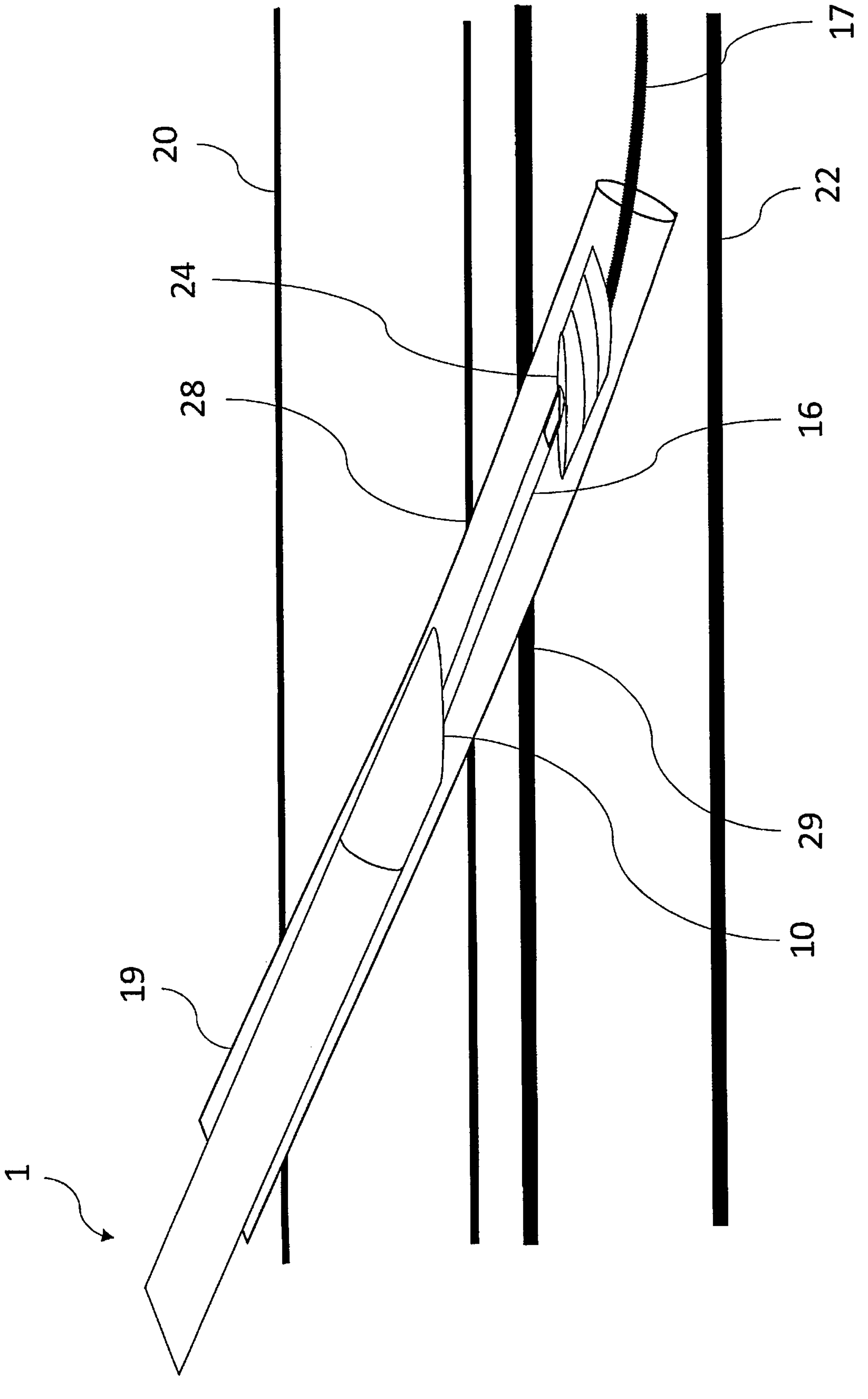
FIG. 8 is a diagram depicting the insertion of the device into the sheath.

The inventive method of fistula creation continues with the advancement of sheath 19 as shown in FIG. 7*c* and as described in block 42 of FIG. 13. Sheath 19 is preferably a design with a very thin wall that continuously tapers to a cross-sectional dimension of nearly nothing at its distal tip. It is also very lubricious. Terumo's 6F Radial Artery Sheath "Glide Sheath Slender" is an exemplary example. Such a sheath can, in concert with an appropriate dilator, dilate a vessel wall while imparting minimal stress to the dilated tissues. This is important in that it minimizes tearing and also maximizes tissue recovery.

Room is then created for device 1 inside of sheath 19 by the removal of dilator 27 and as described in block 42 of FIG. 13. Guidewire 17 may or may not be removed at this point as well. This is a safety issue left up to the practitioner. Device 1 is then inserted into the patient by loading into the proximal end of sheath 19 and optionally over guidewire 17. The device 1 is advanced further into the patient until inner tube 16 is centered at the anastomosis site as in FIG. 8 and as described in block 44 of FIG. 13.

Ultrasound and/or fluoroscopy is used at this point to determine where tube 16 is relative to vessels 20 and 22. Ultrasound doesn't have the resolution and depth to indicate where the vessel walls are in relation to the embedded heater 12 face and heat spreader 24 faces. Manipulation of the device without a sheath can unknowingly move vessels around and actually get them intertwined and folded around device 1, especially around tube 16 and the proximal edge of heat spreader 24. These dynamics are hard to track under ultrasound and may go unnoticed. Proceeding with the cutting and welding on such unorganized tissue does not produce a viable fistula.

Because sheath 19 and dilator 27 do not disrupt vessels 20 and 22, this alignment is easier to approximate while device 1 is inside sheath 19. Alignment with the sheath in place avoids moving vessels around with device 1, as it is isolated from the vessels by the sheath. Adjustments to the relative placement of device 1 with vessels 20 and 22 do not move vessels 20 and 22 and are, therefore, not stressed. Less movement of the vessels, especially at openings 28 and 29, mean less stress imparted on the vessel openings. This minimizes tearing and maximizes elastic recovery and promotes improved coaptation for welding and cutting. The method of fistula creation continues by retracting sheath 19 and as described in block 46 of FIG. 13. Because sheath 19 has a very lubricious un-interrupted tapering outer surface, it can be removed without disturbing the alignment of inner tube 16 to the fistula site. Vessel openings 28 and 29 have not been overly stressed and elastically recover to seal around inner tube 16. A slight tension is applied to the embedded heater 12 to seat it against the vessel wall and promote vessel apposition. The blunt shape of the heat spreader 24 on the distal tip 5 prevents the distal tip from inadvertently retracting back through the vessel wall. The heat spreader 24 of the distal heating assembly 4 is then retracted to close the spacing between until the walls of the first and second vessels 20 and 22, respectively, are captured between the facing blunt surfaces of embedded heater 12 and distal heat spreader 24.

The method of fistula formation continues, as described in block 48 of FIG. 13, by applying a controlled tension between distal tip 5 and proximal base 10, and at this juncture, with the vessels securely clamped, energy is applied to proximal heating element 8. As embedded heater 12 heats up, rib 9 cuts through the vessel walls and embedded heater 12 will contact heat spreader 24. When fully retracted, the system is designed so that the two heating elements come into direct contact with one another to ensure a complete cut and capture of the vessel tissue.

Fistula formation continues, as described in block 48 of FIG. 13. After vessel walls are cut, rib 9 now contacts heat spreader 24 to conduct heat into the spreader for the purposes of welding the vessels together. Rib 9 floats inside of the rib relief 15 on heat spreader 24. Heat spreader 24 is spring loaded by both resilient member 26 (FIG. 1*b*) and spring tension on inner tube 16 to ensure proper pressures are maintained for tissue welding. Two springs are desirable because of the uncertain forces transmitted through tube 16. Tube 16 has high normal frictional forces imposed by angle θ which can be influenced by the variable coefficient of friction between tube 16 and proximal shaft 2. This coefficient of friction will change based on fluids within the fistula, tolerances within device 1, and the progress of coagulation of blood within the interface. This friction can vary by as much as a factor of 8. Resilient member 26 acts directly on the tissue interface with no frictional interference. This enables better assurance that the proper pressures are imparted on the tissues while welding.

Regarding the tissue welding process, more particularly, the DC resistive energy functions to fuse or weld the vessels together, creating an elongate aperture 25 (FIG. 12) through the opposing walls of each of the first and second vessels, as well as any intervening tissue. As formed, the elongate aperture may typically resemble a slit. However, as pressurized flow begins to occur through aperture 25, which creates a communicating aperture between the first and second blood vessels, the aperture widens in response to the pressure, taking the shape of an ellipse as it opens to form the desired fistula. The effect is illustrated in FIG. 12. The edges 21 of the aperture are cauterized and welded. Outwardly of the weld band 21 is a coaptation area 23. As shown, the cut area corresponds to the shape of the heating or cutting element. It can be of multiple shapes, such as round, oval, a slit, or a combination as shown. The area adjacent to the cut has been approximated and welded due to the flat face of the catheter in the vein (first vessel) being larger than the embedded heater 12. The heat from the embedded heater 12 is also preferably spread over this area by a conductive material that can be above, below or within the embedded heater 12 or base 10.

Figure 11:
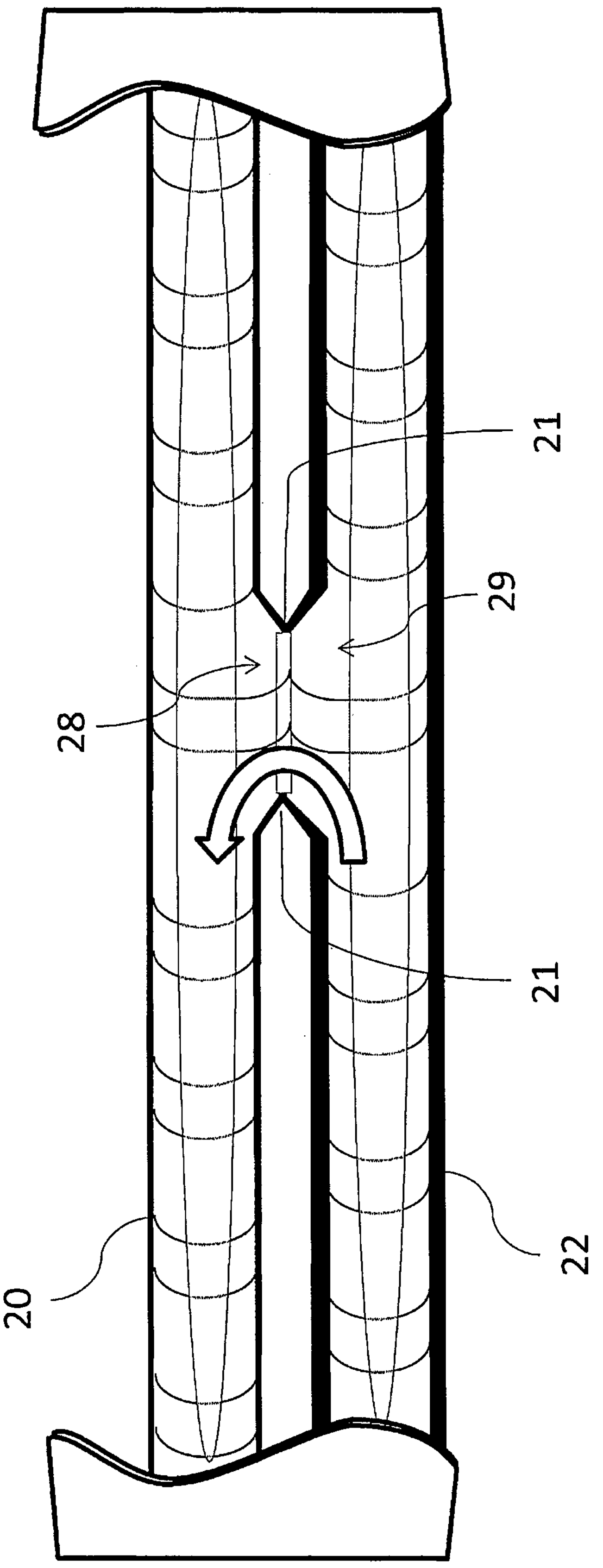
FIG. 11 is a diagram showing the flow through vessels as a result of the device's service.

Now that fistula 25 has been fully formed, as described in block 50 of FIG. 13, the entire instrument 1 and, optionally, guidewire 17 are withdrawn. Fluid flow is now established between vessels 20 and 22 through fistula 25 as shown in FIG. 11.

In another modified embodiment, embedded heater 12 and heating element 8 may be merged into the same component. The welding and cutting surfaces can be smaller so as to approximate the dimensions of the heating element, making this change practical. The dimensions of heating element 8 will determine the resistance across power attachment points 11. This resistance in relation to the resistance of the leads conducting energy to heater element 8 is critical. As the resistance across points 11 lowers and approximates the resistance in the leads, the leads will start to burn a good portion of the power, heating up proximal shaft 6 and requiring more energy to be delivered to accomplish the same weld. Heating element is made longer by its serpentine shape, thus increasing its resistance to minimize this effect. Choosing a heating element material with greater resistance will also help.

In another modified embodiment, rib relief 15 may be eliminated, and ribs 9 formed to contact a surface on heat spreader 24. The nature of this contact and the shapes of the surfaces may enhance thermal cutting with mechanical cutting. The mechanical cutting may be accomplished by putting sharp edges on the ribs that interact with heat spreader 24 so as to shear tissue. Heat spreader 24 may also have surfaces or edges that work in concert with features on ribs 9 to mechanically cut tissue. These cutting designs maximize the final contact area between ribs 9 and the heat spread so that sufficient heat transfer is available to the spreader to weld tissues together in the next step.

Welding is possible without resilient member 26 and rib relief 15. Tissue will be trapped in a gap controlled by the height of rib 9. The compliance of tissue within that gap will dictate the pressure under which it is welded. In some designs and applications, this is sufficient.

The distal tip 5 can have a uniform conical tapered outer surface, though it can have a variable tapered, sloped outer surface, wherein the outer surface tapers down to the approximate diameter of a guidewire to provide an atraumatic method for passing through the vessel wall. This is especially desirable if sheath 19 is inadvertently removed before distal tip 5 is placed in second vessel 22 and may be viewed as a safety feature. The choice to use this embodiment may be influenced by practitioner skills and experience, anatomy, or patient health.

Device 1 does not require guidewire 17 for placement within sheath 19 as sheath 19 provides secure placement. Consequently, device 1 need not contain provisions for advancement over the guidewire such as lumen 18. Lumen 18 might still exist and serve as a conduit for the transport of materials used in the creation of the fistula such as drugs, biologic fluids, or an adhesive.

Energy settings may change to weld tissues at other temperatures. Energy may be modulated based upon the impedance of the tissue or temperature feedback. Different energy application durations, or cyclic pulses may be used to maximize welding while minimizing heat transfer to adjacent tissues. The distal tip 5 is configured to have insulating properties to minimize heat transfer to adjacent tissues and/or fluids. As noted above, the entire surface of the proximal and distal heat elements is configured to have a non-stick coating, such as PTFE, to limit tissue adhesion.

It is advantageous for the proximal and distal heating assemblies 2 and 4 to have a non-stick surface to prevent denatured tissue from bonding to the device. If tissue bonds to the device, the weld between vessels can be damaged or weakened during removal of the device. Multiple different coatings or surface modifications can be applied to the components to create a non-stick surface.

In the embodiment of FIG. 3, it is advantageous that an inner tube 16 also have a non-stick surface to prevent coagulated blood and tissue from bonding to the surface and obstructing the annular gap between the outside diameter of the inner tube 16 and the inside diameter of the proximal heating assembly 2. If blood or tissue bonds to or obstructs this annular gap, this may prevent effective compressive force transmission to the distal heating assembly 4 and compromise tissue weld fusion or tissue cutting.

The compression force of the distal heating assembly 4 influences the weld quality of the tissue. If too much pressure is applied, distal heating assembly 4 may quickly cut through the tissue. A balance of heat and pressure is required to desiccate and denature the protein in the tissue to promote adhesion. In order to best achieve this, resilient member 26 is placed behind heat spreader 24. Resilient member 26 may be pre-compressed in its placement between heat spreader 24 and distal tip 5. This will enable resilient member 26 to best approximate a linear force thus ensuring the proper pressure is applied to tissue during welding. Resilient member 26 is preferably made out of silicone. Common compression springs could also be used coiled or Belleville springs made out of bio-compatible materials.

In one embodiment, the lumen 18 is sized to receive a 0.014-inch guidewire, but may be sized to receive guidewires of various diameters. Larger and smaller guidewires are sometimes preferred. Larger diameter guidewires offer more support to transport devices and resist prolapsing. Smaller guidewires are less likely inadvertently penetrate tissues and can navigate tortuosities easier. Such dynamics are known to those familiar with the art.

In one embodiment, the proximal base 10 is cut at an angle θ of 23 degrees, forming a distal diagonal end surface 10*a*. However, the angle θ can be adjusted depending on the particular anatomy of a procedural site and desired anastomosis length. The inventors have found that the angle θ provides advantageous outcomes within a range of about 15-90 degrees, and more particularly within a range of 15-50 degrees, keeping in mind that approximately 23 degrees is presently a particularly preferred angle within that range. These preferred angles/angle ranges result in an optimized oval configuration for the anastomosis which maximizes the cutting surface while also efficiently utilizing available heating energy to create an effective cut and welding zone.

A variety of DC resistive energy profiles may be used to achieve the desired cutting. For example, a rapidly stepped or ramped increase to achieve and maintain a desired temperature setting of 150° C.-600° C. may be applied to cut through the vessel walls.

Regarding materials, in one preferred embodiment, the outside diameter of the inner tube 16 and inside diameter of the proximal heating assembly 2 have a surface finish of <16 Ra, have an annular gap of 0.0005-0.0002 inches, and are coated using a high temperature Parylene. Other non-stick coatings, such as Poly Tetra Fluoro Ethylene (PTFE), Titanium Nitride (TiN), Chromium Nitride (CrN), Dicronite, silicone, or other similar coatings known to those skilled in the art may be used to prevent tissue adherence.

Materials known to work well for proximal base 10 and shaft 4 include Vespel, Celazol, Teflon, Polyimide, Ultem, and ceramics.

Examples of thermally conductive material suitable for the construction of embedded heater 12, and ribs 9, and heat spreader 24 include aluminum, stainless steel, aluminum nitride, or other metal or ceramic materials known to those skilled in the art.

Accordingly, although an exemplary embodiment and method according to the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. An apparatus, comprising:

a first tissue weld member having a thermally conductive first contact surface including a surface portion and a rib extending outwardly therefrom, the first contact surface being configured to contact a surface of a first tissue wall, the first tissue weld member including an electrical heating element beneath the surface portion and the rib of the first contact surface, wherein the electrical heating element is in thermal contact with the first contact surface to enable heat transfer from the electrical heating element to the first contact surface;

a tubular member coupled to the first tissue weld member, the tubular member configured to operatively couple the electrical heating element to a power supply; and a second tissue weld member having a second contact surface defining a rib receival space configured to receive the rib, the second contact surface being configured to contact a surface of a second tissue wall, the second contact surface configured to be aligned with the first contact surface to position the surface of the first tissue wall and the surface of the second tissue wall between the first contact surface and the second contact surface such that when a current is conveyed from the power supply to the electrical heating element, the first tissue wall and the second tissue wall are welded together.

2. The apparatus of claim 1, wherein the power supply is configured to control the current to produce a heat flow between the surface of the first tissue wall and the surface of the second tissue wall sufficient to denature a protein in at least one of the first tissue wall or the second tissue wall.

3. The apparatus of claim 1, wherein:

the surface portion extends around the rib; and the second contact surface includes a surface portion extends around the rib receival space.

4. The apparatus of claim 3, wherein the rib is configured to cut into the first tissue wall and the second tissue wall.

5. The apparatus of claim 1, wherein the first tissue weld member and the second tissue weld member are configured to be compressed against each other to exert a compression force against the first tissue wall and the second tissue wall.

6. The apparatus of claim 5, wherein the second tissue weld member is configured to maintain the compression force within a range.

7. The apparatus of claim 1, wherein the surface portion is substantially flat.

8. The apparatus of claim 1, wherein the first tissue weld member includes an opposite surface opposite the first contact surface, wherein the opposite surface defines a channel in which the electrical heating element is received.

9. The apparatus of claim 8, wherein the electrical heating element is embedded in the channel.

10. The apparatus of claim 9, wherein the channel has a channel geometry and the electrical heating element has a heating element geometry matching the channel geometry such that the heating element interlocks within the channel.

11. The apparatus of claim 8, wherein the channel geometry and the heating element geometry comprise serpentine geometries.

12. The apparatus of claim 11, wherein the apparatus is configured to form the fistula with an edge and a coaptation region surrounding the edge.

13. The apparatus of claim 12, wherein the edge has a serpentine geometry and the coaptation region has an ovoid geometry.

14. The apparatus of claim 8, wherein the apparatus is configured to be inserted into a first bodily lumen of a subject, wherein the first tissue wall is a tissue wall of the first bodily lumen and the second tissue wall is a tissue wall of a second bodily lumen, and wherein the apparatus is configured to form a fistula enabling fluid communication between the first bodily lumen and the second bodily lumen.

15. A method of performing a surgical procedure using the apparatus of claim 1, comprising:

advancing the tubular member within a first blood vessel;

moving the second tissue weld member within a second blood vessel to align the first contact surface of the first weld member with the second contact surface of the second member such that the surface of the first blood vessel and the surface of the second blood vessel are between the first contact surface and the second contact surface;

compressing a portion of the first blood vessel and a portion of the second blood vessel between the first contact surface and the second contact surface; and conveying a current to the first weld member to cause a heat flow between the first contact surface and the second contact surface, the heat flow sufficient to weld the first blood vessel and the second blood vessel together.

16. The method of claim 15, wherein the conveying the current produces the heat flow sufficient to achieve a temperature within the portion of the first blood vessel and the portion of the second blood vessel of between about 150 degrees Celsius and 600 degrees Celsius.

17. The method of claim 15, wherein the moving the second tissue weld member within the second blood vessel includes aligning the rib with the rib receival space, a shape of the rib corresponding to a shape of the rib receival space.

18. The method of claim 17, wherein:

the shape of the rib and the shape of the rib receival space are substantially rectangular; and the moving the second tissue weld member includes moving the rib at least partially within the rib receival space.

19. The method of claim 15, wherein the compressing the portion of the first blood vessel and the portion of the second blood vessel includes limiting a compression force exerted against the first blood vessel and the second blood vessel.

20. The method of claim 15, further comprising:

moving the first tissue weld member away from the portion of the first blood vessel; and moving the second tissue weld member away from the portion of the first blood vessel, the first contact surface and the second contact surface including a coating formulated to reduce tissue adherence.

* * * * *